United States Patent
Saulys et al.

(10) Patent No.: US 7,319,159 B1
(45) Date of Patent: Jan. 15, 2008

(54) CYCLOHEXADIEN-2,4-YLSILANE AND ITS DERIVATIVES, SYNTHESIS OF THE SAME, AND THE PYROLYSIS OF THE SAME TO SILANE

(75) Inventors: Dovas A. Saulys, Seoul (KR); Thomas F. Kuech, Madison, WI (US); John A. Roberts, Chicago, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/531,650

(22) Filed: Sep. 13, 2006

(51) Int. Cl.
*C07F 7/08* (2006.01)
(52) U.S. Cl. ............... 556/465; 556/487; 556/489
(58) Field of Classification Search ............ 556/465, 556/487, 489
See application file for complete search history.

(56) References Cited

U.S. PATENT DOCUMENTS

| | | | | |
|---|---|---|---|---|
| 2,820,048 | A | * | 1/1958 | Pines et al. ............ 556/475 |
| 4,676,967 | A | | 6/1987 | Breneman |
| 5,271,908 | A | | 12/1993 | Shiban et al. |
| 6,103,942 | A | | 8/2000 | Tsuo et al. |

OTHER PUBLICATIONS

Saulys et al., "Point-of-Use Silicon Sources for CVD", Mater. Res. Soc. Symp. Proc. (1997), 447, 139.
Abstract by SciFinder Scholar for Ottosson et al., "The Tris(9-borabicyclo[3.3.1]nonyl)silylium Catlon", Organometallics (1997), 16(11) 2377-2385.
Abstract by SciFinder for Nicolaides et al., "Relative Stabilities and Hydride Affinities of Sila-tropylium and Sliabenzyl Cations & Their Isomers", J.Am.Chem.Soc. (1996) 118(43), 10561-10570.
Abstract by SciFinder Scholar for Olsson et al., "Evidence for the Existence of Silylium Cations in Condensed Phases", Chem. Phys. Lett. (1993) 215(5), 433-43.
Abstract by SciFinder Scholar for Schleyer at al., "The Search for an Isolable Silyl Cation Must Go On", Angew. Chem. (1993), 105(10), 1558-61.
Abstract by SciFinder Scholar for Baxter et al., "Multihapto Bonding Between Main Group Elements and Carbocyclic Ligands", ACS Symp. Ser. (1983), 232, 111-23.

* cited by examiner

*Primary Examiner*—Porfirio Nazario-Gonzalez
(74) *Attorney, Agent, or Firm*—Quarles & Brady LLP

(57) ABSTRACT

Silane gas precursor compounds having the formula (I):

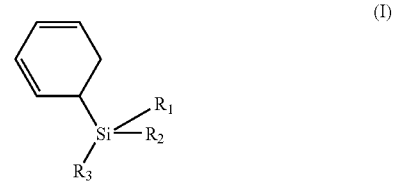

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and $C\equiv N$ are disclosed. In one form, the silane gas precursor compound is cyclohexadien-2,4-ylsilane, an air-stable liquid, that can be thermolyzed in a pyrolysis process to efficiently generate high purity silane gas. The compounds of the present invention can thus serve as a "point-of-use" precursor for silane gas.

20 Claims, 1 Drawing Sheet

CYCLOHEXADIEN-2,4-YLSILANE AND ITS DERIVATIVES, SYNTHESIS OF THE SAME, AND THE PYROLYSIS OF THE SAME TO SILANE

STATEMENT REGARDING FEDERALLY SPONSORED RESEARCH OR DEVELOPMENT

This invention was made with United States government support awarded by the following agencies: NSF 9632527. The United States has certain rights to this invention.

CROSS-REFERENCE TO RELATED APPLICATIONS

Not applicable.

BACKGROUND OF THE INVENTION

The present invention relates to a class of new silane-substituted cycloalkene compounds that are an innocuous, air-stable liquid. These silane-substituted cycloalkene compounds can then, for example, be thermally decomposed to yield high purity silane for point-of-use application in the semiconductor industry.

Many industries use pyrophoric gases for a variety of processes and operations. In the semiconductor industry, a variety of pyrophoric gases are used during the manufacture of semiconductor devices. These gases are termed pyrophoric due to their ability to ignite spontaneously upon contact with an oxidant such as oxygen. Thus, these gases may ignite upon contact with air, and if a pocket of pyrophoric gas contacts air, an explosion may result. The possibility of explosion is increased by the tendency of some pyrophoric gases to "self-protect", wherein bubbles or pockets of the pyrophoric gas develop which prevents reaction or neutralization of the pyrophoric gas in a controlled manner.

Pyrophoric gases are usually used for the deposition of various layers or for introducing dopants into the various layers of a semiconductor device. For example, silane ($SiH_4$) may be used along with oxygen to from a silicon dioxide ($SiO_2$) layer in a chemical vapor deposition (CVD) system. Diborane ($B_2H_6$), phosphine ($PH_3$), and arsine ($AsH_3$) may be used to add dopants to a layer. Silane also is used to form polycrystalline silicon layers as well as epitaxial, single crystal silicon in a variety of processes. Silane gas is an inherently dangerous material in that it is highly volatile and pyrophoric (i.e., it explodes on contact with air). A recent SEMATECH report indicated that on-site accidents involving silane cost the industry over $500K/year (See, e.g., SEMATECH Technology Transfer Report #94062405A-ENG, Silane Safety Improvement Project S71, 1997); and indirect costs (e.g., safety restrictions during transportation and storage, loss of production due to silane-related incidents, etc.) are likely much higher.

U.S. Pat. No. 6,103,942 discloses a method of preparing high purity silane. The process comprises a temperature assisted reaction of metallurgical silicon with alcohol in the presence of a catalyst. Alkoxysilanes formed in the silicon-alcohol reaction are separated from other products and purified. Simultaneous reduction and oxidation of alcoxysilanes produces gaseous silane and liquid secondary products including the active part of a catalyst, tetra-alkoxysilanes, and impurity compounds with silicone-hydrogen bonds. Silane is purified by an impurity adsorption technique.

Another technique for producing high purity silane is described in U.S. Pat. No. 4,676,967. The overall process includes (1) the enhanced production of trichlorosilane from metallurgical silicon and hydrogen, (2) the disproportionation of trichlorosilane to produce high purity silane, and (3) the conversion of said silane to high purity silicon, if desired. The disclosure of all of the above patents and of all other articles and patents cited herein are incorporated herein by reference as if fully set forth herein.

What is needed in the art is a process for making a silane gas precursor which is innocuous and air stable that can be easily and directly decomposed to high purity silane gas for point-of-use in various industrial applications.

SUMMARY OF THE INVENTION

The invention describes a safe alternative to the storage and use of silane. The present invention provides a silane gas precursor compound which is innocuous and air stable that can be easily and directly thermally decomposed to high purity silane gas. The silane gas precursor compound has the formula (I):

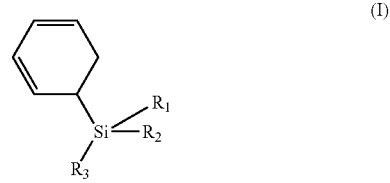

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and $C\equiv N$. In accord with an example embodiment of the invention, cyclohexadien-2,4-ylsilane, an air-stable liquid, is synthesized, then thermolyzed to efficiently generate high purity silane gas. The compounds of the present invention can thus serve as a substitute, or "point-of-use" precursor for silane. The invention thereby enhances safety and improves control in industrial and academic research environments, with attendant savings in safety-related expenditures, and increases productivity due to the elimination of down-time caused by silane-related incidents.

Thus, one aspect of the invention is directed to the synthesis of a new chemical compound that is an innocuous, air-stable liquid. Another aspect of the invention is directed to a pyrolysis process that cleanly generates silane from the compound. The overall purpose of the invention is to enhance safety and improve control in industrial and academic research environments by providing an air-stable, liquid alternative to the highly volatile and pyrophoric silane gas.

These and other features, aspects, and advantages of the present invention will become better understood upon consideration of the following detailed description, drawings, and appended claims.

DETAILED DESCRIPTION OF THE INVENTION

Figure 1:
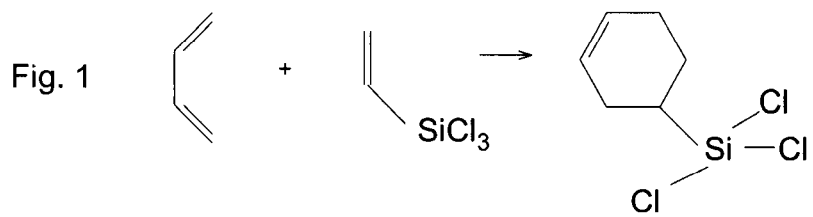
FIG. 1 is a reaction scheme for producing 3-cyclohexenyltrichlorosilane as part of a process according to the invention.

The present invention provides a silane gas precursor compound having the formula (I):

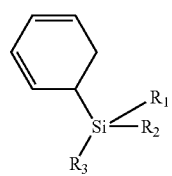

(I)

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and $C\equiv N$. In one form, at least one of $R_1$, $R_2$, and $R_3$ is chlorine. In another form, $R_1$, $R_2$, and $R_3$ are all hydrogen and the cyclohexadiene ring has no substituents. In a preferred form, formula (I) is cyclohexadien-2,4-ylsilane.

In another aspect, the invention provides a process for producing silane wherein a silane gas precursor having the formula (I) is thermally decomposed without oxidation to produce silane. Preferably, the thermal decomposition is carried out at a temperature at which silane does not decompose, for example, a temperature in the range of 400° C. to 500° C. In one version of the process, the silane is separated by fractionation from benzene formed in the thermal decomposition. In a preferred version, cyclohexadien-2,4-ylsilane is thermally decomposed in a pyrolysis process to silane.

In another aspect, the invention provides a process for producing an air-stable, liquid, substituted or unsubstituted silane precursor. In the process, a compound having the formula (III)

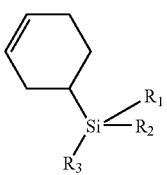

(III)

wherein the $R_1$, $R_2$, and $R_3$ are hydrogen or halogen, and wherein the cyclohexene ring can have one or more substituents selected from the group consisting of a saturated or unsaturated, straight chain or branched alkyl group, a halogen, $NO_2$, and $C\equiv N$, is halogenated to form the compound of formula (II):

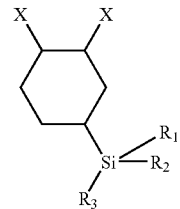

(II)

wherein the $R_1$, $R_2$, and $R_3$ are hydrogen or halogen. The compound of formula (II) is dehydrohalogenated to form a silane precursor compound having the formula (I):

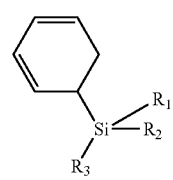

(I)

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and $C\equiv N$. In one version of this process, at least one of the $R_1$, $R_2$, and $R_3$ of Formula (III) is halogen and Formula (III) is reduced before halogenation. In another version of this process, the $R_1$, $R_2$, and $R_3$ of Formula (III) are all chlorine and the process includes reducing Formula (III) before halogenation. In yet another version of this process, the $R_1$, $R_2$, and $R_3$ of Formula (III) are all chlorine and the cyclohexene ring of Formula (III) has no substituents. In still another version of this process, X of Formula (II) are all bromine. In yet another version of this process, the $R_1$, $R_2$, and $R_3$ of Formula (I) are all chlorine and the cyclohexadiene ring of Formula (I) has no substituents. In a preferred version of this process, the $R_1$, $R_2$, and $R_3$ of Formula (III) are all chlorine, the cyclohexene ring of Formula (III) has no substituents, the process further comprises reducing Formula (III) before halogenation, the X of Formula (II) are all bromine, the $R_1$, $R_2$, and $R_3$ of Formula (I) are all chlorine, and the cyclohexadiene ring of Formula (I) has no substituents. In a preferred form, formula (I) is cyclohexadien-2,4-ylsilane.

In yet another aspect, the invention provides an intermediate used in the production of a silane precursor compound having the formula (I):

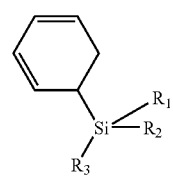

(I)

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, NO$_2$, and C≡N. The intermediate is a compound having the following formula (II):

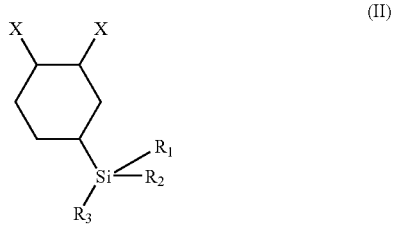

wherein R$_1$, R$_2$, and R$_3$ of formula (II) each can independently be hydrogen or halogen, wherein X is halogen, and wherein the ring of formula (II) can have one or more substituents selected from the group consisting of a saturated or unsaturated, straight chain or branched alkyl group, a halogen, NO$_2$, and C≡N. In one form, each X is bromine. In another form, at least one of R$_1$, R$_2$, and R$_3$ of formula (II) is chlorine. In yet another form, R$_1$, R$_2$, and R$_3$ of formula (II) are all hydrogen and the ring of formula (II) has no substituents. The intermediate is preferably 3,4-dibromocyclohexenylsilane.

Figure 2:
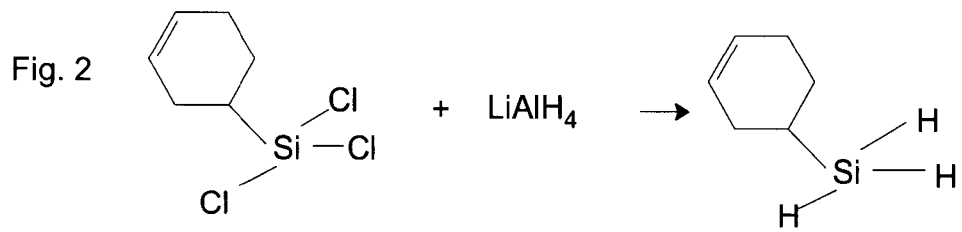
FIG. 2 is a reaction scheme for producing 3-cyclohexenylsilane as part of a process according to the invention.
Figure 3:
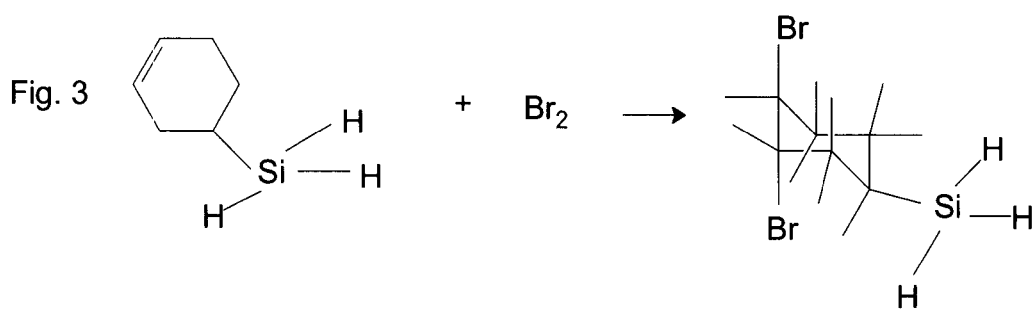
FIG. 3 is a reaction scheme for producing 3,4-dibromocyclohexenylsilane as part of a process according to the invention.
Figure 4:
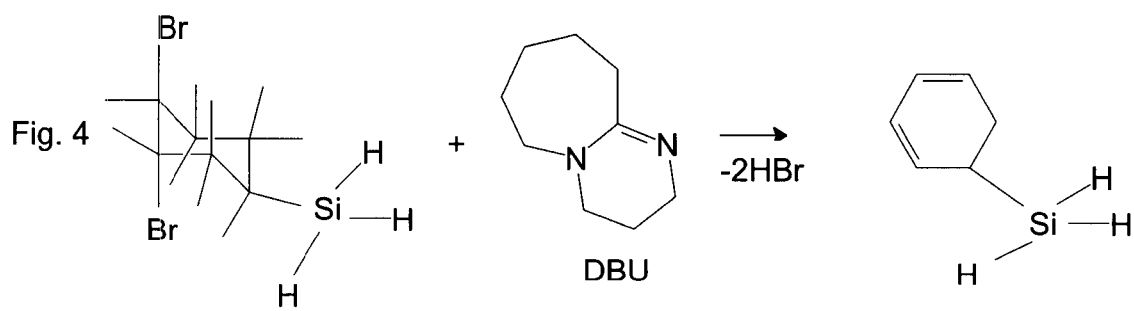
FIG. 4 is a reaction scheme for producing cyclohexadien-2,4-ylsilane from 3,4-dibromocyclohexenylsilane as part of a process according to the invention.

In one example version of the invention, we designed a multi-step synthesis for the preparation of cyclohexadien-2,4-ylsilane, SiC$_6$H$_{10}$. The commercially available starting material vinyltrichlorosilane was reacted with 1,3-butadiene in a high pressure Diels Adler reaction to generate 3-cyclohexenyltrichlorosilane (see FIG. 1). Then 3-cyclohexenyltrichlorosilane was reduced to 3-cyclohexenylsilane with LiAlH$_4$ in refluxing ether (see FIG. 2). The 3-cyclohexenylsilane was purified by reduced pressure distillation, and then brominated with elemental bromine to 3,4-dibromocyclohexenylsilane (see FIG. 3). The 3,4-dibromocyclohexenylsilane was purified by high volume alembic distillation, then dehydrohalogenated by reaction with an excess of commercially available 1,8-diazabicyclo[5.4.0]undec-7-ene (DBU) in anhydrous dodecane (see FIG. 4). The resulting cyclohexadien-2,4-ylsilane was purified by a reduced pressure distillation on a spinning band column. The intermediate compounds as well as the final product were characterized by their volatility, infra-red (IR) spectroscopy, mass spectrometry, as well as $^1$H, $^{13}$C, and $^{29}$Si nuclear magnetic resonance (NMR) spectroscopy.

Figure 5:
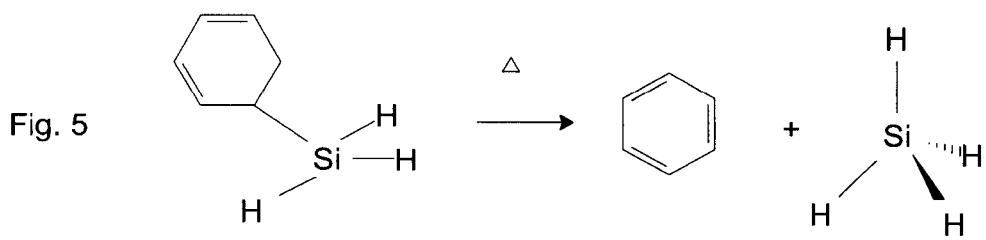
FIG. 5 is a reaction scheme for producing silane from cyclohexadien-2,4-ylsilane as part of a pyrolysis process according to the invention.

The cyclohexadien-2,4-ylsilane was thermally decomposed in a dynamic vacuum process (base pressure: 10$^{-3}$ to 10$^{-4}$ torr), in the absence of carrier gas, at 490° C. to yield silane, SiH$_4$, and benzene (see FIG. 5). Use of a glass high vacuum line makes possible the isolation, and hence the unambiguous identification and quantification of the silane produced. Silane was characterized by its volatility, gas phase IR spectroscopy, and proton and $^{29}$Si NMR spectroscopy.

The following aspects of the thermal decomposition process should be noted. (1) The temperature employed, 490° C., is sufficiently low that the silane produced does not itself undergo any degree of decomposition. Earlier procedures to thermally generate silane from organosilanes required temperatures of between 550° C. and 600° C., temperatures at which the decompositions of silane itself is significant (see, e.g., Saulys et al., "Point-Of-Use Silicon Sources For CVD", Mater. Res. Soc. Symp. Proc. (1997), 447, 139). (2) The generation of silane is a straightforward process, as evidenced by the lack of residue on or discoloration of the pyrolysis apparatus. (3) Given the short residence time of the substrate molecules in the hot zone in the pyrolysis apparatus, the conversion of 8.5% of the cyclohexadien-2,4-ylsilane is extraordinary. Finally, the large difference in boiling points between the organic by-product of the thermolysis reaction, benzene, (boiling point 80.1° C.) and the silane produced (boiling point –111.8° C.) facilitates the separation of high-purity silane gas by fractionation.

It is important to note that previous work by us has shown a general correspondence between results obtained in flow pyrolysis systems using a carrier gas, and dynamic high vacuum systems of the type described here. Thus the results pertaining to the invention are likely general, and do not depend on the specific type of pyrolysis system used.

Thus, the invention provides silane gas precursor compounds having the formula (I):

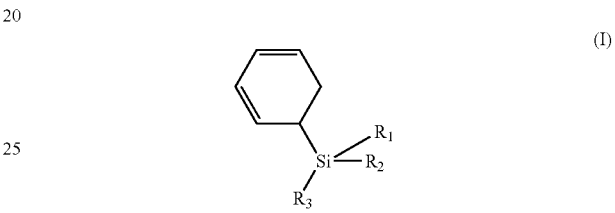

wherein R$_1$, R$_2$, and R$_3$ each can independently be hydrogen or halogen and wherein the cyclohexadiene ring can have one or more substituents selected from the group consisting of a saturated or unsaturated, straight chain or branched alkyl group, a halogen, NO$_2$, and C≡N. In one example form, the silane gas precursor compound is cyclohexadien-2,4-ylsilane, an air-stable liquid, that can be thermolyzed to efficiently generate high purity silane gas. The compounds of the present invention can thus serve as a "point-of-use" precursor for silane gas.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention provides a process for producing silane gas precursor compounds which are innocuous and air stable that can be easily and directly decomposed to high purity silane gas for point-of-use in various industrial applications.

What is claimed is:
1. A compound having the formula (I):

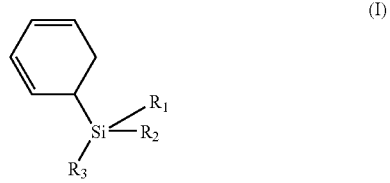

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and $C\equiv N$, wherein at least one of $R_1$, $R_2$, and $R_3$ is hydrogen.

2. The compound of claim 1 wherein at least one of $R_1$, $R_2$, and $R_3$ is chlorine.

3. The compound of claim 1 wherein $R_1$, $R_2$, and $R_3$ are all hydrogen and wherein the cyclohexadiene ring has no substituents.

4. A compound having the following formula (II):

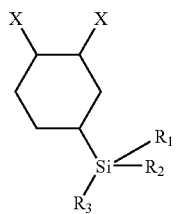

(II)

wherein $R_1$, $R_2$, and $R_3$ each can independently be hydrogen or halogen, wherein X is halogen, and wherein the ring can have one or more substituents selected from the group consisting of a saturated or unsaturated, straight chain or branched alkyl group, a halogen, $NO_2$, and $C\equiv N$, wherein at least one $R_1$, $R_2$ and $R_3$ is hydrogen.

5. The compound of claim 4 wherein X is bromine.

6. The compound of claim 4 wherein at least one of $R_1$, $R_2$, and $R_3$ is chlorine.

7. The compound of claim 4 wherein $R_1$, $R_2$, and $R_3$ are all hydrogen and wherein the ring has no substituents.

8. The compound of claim 4 wherein X is bromine and $R_1$, $R_2$, and $R_3$ are all hydrogen and wherein the ring has no substituents.

9. A process for producing an air-stable, liquid, substituted or unsubstituted silane precursor, the process comprising:

(a) providing a compound having the formula (III)

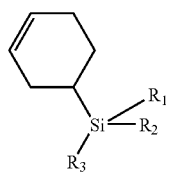

(III)

wherein the $R_1$, $R_2$, and $R_3$ are hydrogen or halogen, and wherein the cyclohexene ring can have one or more substituents selected from the group consisting of a saturated or unsaturated, straight chain or branched alkyl group, a halogen, $NO_2$, and $C\equiv N$;

(b) halogenating the cyclohexene ring of formula (III) to form the compound of formula (II):

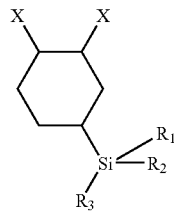

(II)

wherein the $R_1$, $R_2$, and $R_3$ are hydrogen or halogen and X is halogen; and (c) dehydrohalogenating the compound of formula (II) to form a silane precursor having the formula (I):

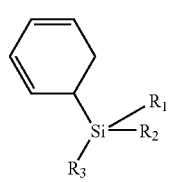

(I)

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and $C\equiv N$.

10. The process of claim 9 wherein at least one of the $R_1$, $R_2$, and $R_3$ of Formula (III) is halogen and the process further comprises reducing Formula (III) before step (b).

11. The process of claim 9 wherein the $R_1$, $R_2$, and $R_3$ of Formula (III) are all chlorine and the process further comprises reducing Formula (III) before step (b).

12. The process of claim 9 wherein the $R_1$, $R_2$, and $R_3$ of Formula (III) are all chlorine and wherein the cyclohexene ring of Formula (III) has no substituents.

13. The process of claim 9 wherein X of Formula (II) are all bromine.

14. The process of claim 9 wherein the $R_1$, $R_2$, and $R_3$ of Formula (I) are all chlorine and wherein the cyclohexadiene ring of Formula (I) has no substituents.

15. A process for producing silane, the process comprising:

(a) providing a compound having the formula (I):

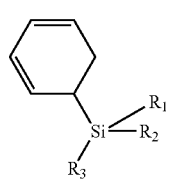

(I)

wherein $R_1$, $R_2$, and $R_3$ each can independently be hydrogen or halogen and wherein the cyclohexadiene ring can have one or more substituents selected from the group consisting of a saturated or unsaturated, straight chain or branched alkyl group, a halogen, $NO_2$, and C≡N; and (b) thermally decomposing the compound to produce silane.

16. The process of claim 15 wherein:

step (b) is carried out at a temperature at which silane does not decompose.

17. The process of claim 15 wherein:

step (b) is carried out at a temperature in the range of 400° C. to 500° C.

18. The process of claim 15 further comprising:

(c) separating by fractionation the silane from benzene formed in the thermal decomposition of step (b).

19. The process of claim 15 wherein:

step (b) is carried out in a vacuum.

20. The process of claim 15 wherein:

step (b) is carried out in the absence of a carrier gas.

* * * * *